(12) United States Patent
Gentry et al.

(10) Patent No.: US 10,815,474 B1
(45) Date of Patent: Oct. 27, 2020

(54) SYSTEM FOR THE 3D CONSTRUCTION OF BIOLOGICALLY DERIVED MATERIALS, STRUCTURES, AND PARTS

(71) Applicant: USA as Represented by the Administrator of the National Aeronautics & Space Administration (NASA), Washington, DC (US)

(72) Inventors: Diana M. Gentry, Atherton, CA (US); Christopher E. Venter, Brisbane, CA (US); Lynn J. Rothschild, Woodside, CA (US)

(73) Assignee: United States of America as Represented by the Administrator of NASA, Washington, DC (US)

(*) Notice: Subject to any disclaimer, the term of this patent is extended or adjusted under 35 U.S.C. 154(b) by 0 days.

(21) Appl. No.: 14/800,238

(22) Filed: Jul. 15, 2015

Related U.S. Application Data

(60) Provisional application No. 62/024,857, filed on Jul. 15, 2014.

(51) Int. Cl.
| | |
|---|---|
| *C12N 11/06* | (2006.01) |
| *C12N 11/10* | (2006.01) |
| *C12N 11/14* | (2006.01) |
| *C12M 1/00* | (2006.01) |
| *C12N 1/18* | (2006.01) |

(52) U.S. Cl.
CPC ............ *C12N 11/06* (2013.01); *C12M 47/00* (2013.01); *C12N 1/18* (2013.01); *C12N 11/10* (2013.01); *C12N 11/14* (2013.01)

(58) Field of Classification Search
CPC .......... C12N 11/06; C12N 11/10; C12N 11/14
See application file for complete search history.

(56) References Cited

U.S. PATENT DOCUMENTS

2005/0088468 A1\* 4/2005 Clark .................. B41J 2/04516
347/11

OTHER PUBLICATIONS

Meeks et al. "Biomaterials out of thin air: in situ, on-demand printing of advanced biocomposites" NIAC 2013 Phase I Final Report.\*
Li et al. "Green Fluorescent Protein in *Saccharomyces cerevisiae*: Real-Time Studies of the GAL1 Promoter" Biotechnology and Bioengineering, vol. 7.\*
NASA "Materials Manufactured from 3D Printed Synthetic Biology Arrays" available on Apr. 30, 2013 at the following website: http://www.nasa.gov/centers/ames/cct/office/cif/2013/3d_synbio.html.\*
3D Printed Build-A-Bone Technology on Display, 3D Printer World, Brooke Kaelin, Jul. 4, 2013 at http://www.3dprinterworld.com/article/3dprinted-build-bone-technology-display.

(Continued)

*Primary Examiner* — Louise W Humphrey
*Assistant Examiner* — Stephen A Perkins
(74) *Attorney, Agent, or Firm* — Rhys W. Cheung; Meredith K. Blasingame; Robert M. Padilla

(57) ABSTRACT

This system combines 3D printing technology with artificially modified cells for production of nonliving biomaterials. A 3D printer deposits a 3D array of bioengineered cells in the shape of a selected product. The cells are programmed to produce biomaterials in regulated amounts. The cell array deposits biomaterials onto a substrate. The cells and substrate are then removed, leaving a finished, nonliving product with microscale structure and precision.

18 Claims, 3 Drawing Sheets

(56) References Cited

OTHER PUBLICATIONS

3D Printer Trumps Pig Parts for Kidney Replacements, 3D Printer World, Brooke Kaelin, Jun. 20, 2013 at http://www.3dprinterworld.com/article/3d-printer-trumps-pig-parts-for-kidney-replacements.

25th Anniversary Article: Engineering Hydrogels for Biofabrication, Wiley Online Library, Malda—Aug. 23, 2013 at http://onlinelibrary.wiley.com/doi/10.1002/adma.201302042/abstract.

How 3D Printing Can Build New Bone, Live Science, Tanya Lewis, Jul. 1, 2013 at http://www.livescience.com/37870-3d-printingrepairs-bone.html.

Is Eco-Friendly 3D Printing a Myth? Live Science, Melba Kurman, Triple Helix Innovation and Hod Lipson, Cornell University, Jul. 20, 2013 at http://www.livescience.com/38323-is-3dprinting-eco-friendly.html.

Manufacturing the Future: The next era of global growth and innovation, McKinsey & Company, Manyika, sinclair, Dobbs, Strube, Rassey, Mischke, Remes, Roxburgh, George, O'Halloran and Ramaswamy, Nov. 2012 at http://www.mckinsey.com/insights/manufacturing/the_future_of_manufacturing.

MIT Mediated Matter Group, Mit Media Lab, http://www.media.mit.edu/research/groups/mediated-matter.

Rapid prototyping in tissue engineering: challenges and potential, Trends in Biotechnology, Yeong, Chua, Leong and Chandrasekaran, vol. 22, Issue 12, p. 643-652, Dec. 2004 at http://www.sciencedirect.com/science/article/pii/S0167779904002926.

\* cited by examiner ical Field or Field of the Invention

SYSTEM FOR THE 3D CONSTRUCTION OF BIOLOGICALLY DERIVED MATERIALS, STRUCTURES, AND PARTS

CROSS-REFERENCE TO RELATED APPLICATIONS

This application claims the benefit of U.S. Provisional Application No. 62/024,857, filed Jul. 15, 2014, which is hereby incorporated herein by reference in its entirety.

ORIGIN OF THE INVENTION

The invention described herein was made in performance of work under a NASA contract and by employees of the United States Government and is subject to the provisions of Public Law 96-517 (35 U.S.C. § 202) and may be manufactured and used by or for the Government for governmental purposes without the payment of any royalties thereon or therefore.

BACKGROUND OF THE INVENTION

Technical Field or Field of the Invention

This invention relates to a system for construction of three-dimensional biomaterials. Cells are engineered to produce materials they do not normally make, or to make natural materials at rates, in quantities, or in combinations they do not naturally perform. The engineered cells are positioned in predetermined patterns so the biomaterials they produce result in biomaterial products.

Description of the Prior Art

Biomaterials, which are defined herein as the non-living materials produced by or integrated into living systems, are advantageous for many applications because they can be produced from limited starting resources, have the potential for high functional customization, and often exceed the performance of known synthetic substitutes. Slow, resource-intensive, and variable production methods, however, currently limit their use. A controlled, on-demand method of producing custom-designed biomaterials and biomaterial products would provide a vast new set of complex building materials.

There are four key problematic characteristics of existing biomaterial production. Speed and scale of production are problems because, although some simple biomaterials—such as cellulose—can be grown in quantity in a matter of hours, more complex biomaterials (e.g., wood and wool), and particularly those with inorganic components (e.g., bone and shell), typically need days, months, or years to be produced on a meaningful scale. A biomaterial used in manufacturing should be relatively easy to produce in mass quantities.

Production overhead is a problem because the minimum material requirements for producing most biomaterials include not only the living organism and the biomaterials' components but the requirements for the organism's support, and, in a complex system, a complete ecosystem may be necessary. The produced biomaterial is typically a very small percentage of the mass required for production. The additional resources required to produce the biomaterial should be reasonable in light of the biomaterial's value.

Reproducibility is another problem for production of biomaterials. All but the simplest biomaterials suffer from macroscale natural variances, and many are heterogeneous, anisotropic, or both. Wood and bone are familiar examples. It is not currently possible to control the growth of a tree at the cellular level to produce uniform, regular timber, much less specific grain patterns designed to strengthen a particular part. To be useful, a biomaterial's macro- and micro-scale properties should be controllable via the production process.

Design and crafting compatibility are still another problem for production of biomaterials. The biomaterials with the most promising properties typically have complex secondary, tertiary, and even quaternary structures, giving them scale- and directionally-dependent properties that provide significant challenges to being machined or incorporated into mixtures or composites. Tools for producing novel, synthetic biomaterials from a selected design are nearly completely absent. A system for production of biomaterials should work them into a finished part or an intermediate material, such a laminate or composite.

In view of the foregoing, it will be appreciated that providing methods and systems for production of biomaterials that allow fast, controlled production of natural, synthetic, and novel biomaterials with minimum resource overhead and reduced pre- and post-processing requirements would be a significant advancement in the art.

SUMMARY OF THE INVENTION

It is a feature of illustrative embodiments of the present invention to provide a method and a system for three-dimensional construction of biologically derived materials, structures, and parts.

These and other features can be addressed by providing a method for producing a three-dimensional biomaterial product, the method comprising:

(A) depositing, into a predetermined three-dimensional pattern on a substrate using a three-dimensional positioning and dispensing system, living cells that are configured for secreting, sequestering, or otherwise producing a selected biomaterial;

(B) immobilizing the deposited living cells such that the predetermined three-dimensional pattern is maintained;

(C) incubating the immobilized living cells under conditions wherein the selected biomaterial is produced;

(D) binding the biomaterial to the substrate;

(E) separating the cells from the bound biomaterial to result in the three-dimensional biomaterial product.

The substrate can be an exogenous material or can be a previously deposited layer of the same or a different biomaterial. In an illustrative embodiment of the present invention, the biomaterial is expressed by an inducible promoter, such as a galactose promoter.

In another illustrative embodiment of the present invention, the living cells comprise *Saccharomyces cerevisiae*.

In still another illustrative embodiment of the present invention, the method of delivery of the material to the cell-external environment comprises secretion by means of a prepended pre-pro-peptide.

In yet another illustrative embodiment of the present invention, the binding of the biomaterial to the substrate comprises polyhistidine-metal binding, antibody-antigen binding, protein-protein binding, or protein-polysaccharide binding.

In still another illustrative embodiment of the present invention, separating the cells from the bound biomaterial comprises washing the bound biomaterial.

In another illustrative embodiment of the present invention, the method further comprises:

(F) separating the biomaterial product from the substrate.

The biomaterial can comprise a protein, a polysaccharide, an inorganic compound, or other materials according to other illustrative embodiments of the present invention.

Additional features can be addressed by providing a system for producing a three-dimensional biomaterial product, comprising:

a computer comprising a processor, a memory coupled to the processor, an input device coupled to the process, and a display coupled to the processor;

a dispenser coupled to the computer, wherein the dispenser comprises a reservoir for receiving a cell culture therein, and a dispenser tip in liquid communication with the reservoir for receiving the cell culture and dispensing a selected volume thereof;

a positioner coupled to the computer, the positioner comprising a stage for receiving a substrate, wherein the positioner is configured for positioning the substrate in selected X, Y, and Z positions with respect to the dispenser tip;

a substrate disposed on the stage, wherein the substrate is configured for receiving the selected volume of cell culture dispensed by the dispenser and for binding a selected biomaterial;

the cell culture, wherein the cell culture comprises living cells configured for producing the selected biomaterial and wherein the cell culture is disposed in the reservoir in a print medium having a viscosity configured for being dispensed by the dispenser and for immobilizing the living cells on the substrate after being dispensed;

the memory having stored therein a set of computer readable instructions that, when executed, cause the processor to perform the operations of:

establishing an interface for receiving instructions from a user based on selecting a volume of cell culture to be dispensed by the dispenser tip, timing of dispensing the selected volume by the dispenser tip, and the X, Y, and Z positions of the stage when the selected volume is dispensed by the dispenser tip;

based on instructions from the user, positioning the stage relative to the dispenser tip; and based on instructions from the user, dispensing the selected volume of cell culture by the dispenser tip.

DETAILED DESCRIPTION OF THE INVENTION

Figure 1:
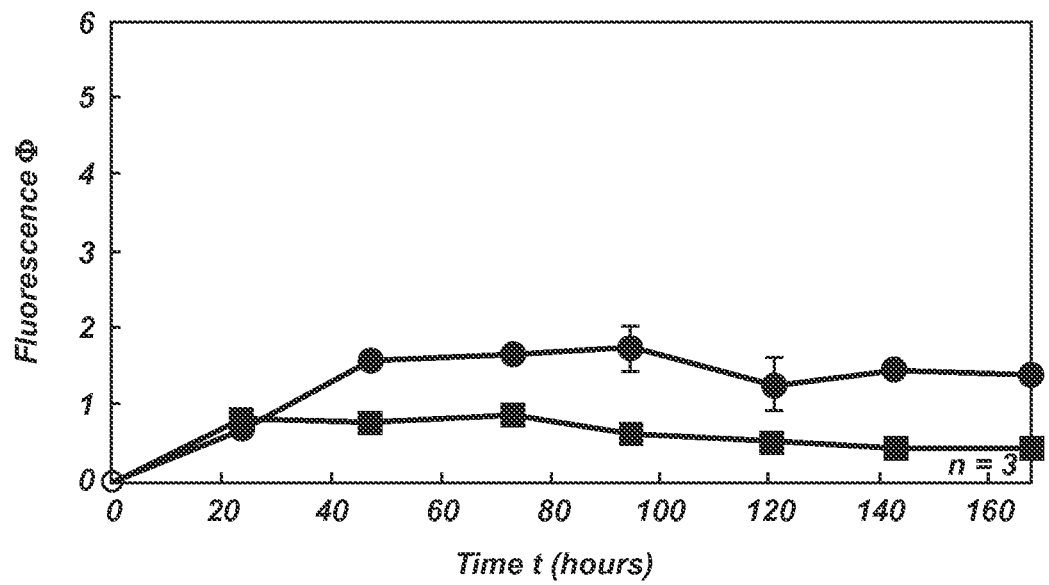
FIG. 1 shows extracellular RFP (red fluorescent protein) expression in transformed *Saccharomyces cerevisiae* cells as a function of time in the presence of dextrose (■) or galactose (●).

Before the present method and system for the 3D construction of biologically derived materials, structures, and parts are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

The publications and other reference materials referred to herein to describe the background of the invention and to provide additional detail regarding its practice are hereby incorporated by reference. The references discussed herein are provided solely for their disclosure prior to the filing date of the present application. Nothing herein is to be construed as an admission that the inventors are not entitled to antedate such disclosure by virtue of prior invention.

It must be noted that, as used in this specification and the appended claims, the singular forms "a," "an," and "the" include plural referents unless the context clearly dictates otherwise. Thus, for example, reference to "a biomaterial" includes a mixture of two or more biomaterials, reference to "an inorganic compound" includes reference to one or more of such inorganic compounds, and reference to "the cells" includes reference to a mixture of two or more of such cell strains or types.

Unless defined otherwise, all technical and scientific terms used herein have the same meanings as commonly understood by one of ordinary skill in the art to which this invention belongs.

In describing and claiming the present invention, the following terminology will be used in accordance with the definitions set out below.

As used herein, "comprising," "including," "containing," "characterized by," and grammatical equivalents thereof are inclusive or open-ended terms that do not exclude additional, unrecited elements or method steps.

According to illustrative embodiments of the present invention, living cells are genetically modified to produce selected biomaterials. The population of engineered cells is multiplied and used as the "ink" in a 3D printer. The 3D printer deposits minute droplets of the cells onto a substrate's surface in a predetermined pattern. Additional passes with the printer augment the thickness of the resulting cell array. The deposited cells are immobilized on the substrate in the predetermined pattern. The cells are fed nutrients, activating agents, and reagents. The activating agents activate the genetically modified genes within the cells to produce the selected biomolecules. The biomolecules accumulate inside the cells, on the outside of cells, or, if secreted, in the spaces between cells. The cells are removed and the biomolecules are bound to the substrate in the predetermined pattern. The resulting non-living, three-dimensional biomolecule product can then be removed from the substrate to result in the finished product.

Biomaterials range in size from a single nanometer for simple molecules like sugars to trees that can reach 100 meters in height. They range in complexity from largely amorphous soft matrices to highly structured, multi-layer composites of organic and inorganic constituents. Examples of naturally occurring biomaterials include saccharides, polysaccharides, amino acids, proteins, cytoskeletal fibers, silk from silkworms and spiders, shell from crustaceans and mollusks, feather from birds, tooth enamel from vertebrates, cartilage from animals, horn and hoof from vertebrates, bone and scale from vertebrates, and wood from plants.

The present disclosure discloses the making of biomaterials through 3D microdeposition and micropositioning technology coupled with genetic engineering of appropriately selected cells. Examples disclose the making of relatively simple biomaterials according to the principles of the present invention.

Host Cell Selection

In selecting a host cell, it is advantageous to use functional cellular units (single cells, unicellular organisms, or activated clusters of cells with a unified function, as in multicellular tissues) to be no smaller than the printing system's resolution. This allows a resolution of one functional cellular unit per voxel in constructing cellular arrays.

Many structural biomaterials are made by multicellular organisms, all of which are eukaryotes. Although genetic engineering of prokaryotes is generally much simpler than of eukaryotes, and prokaryotes may be used as host cells according to illustrative embodiments of the present invention, the range of biomaterials that are naturally made in eukaryotes suggests that eukaryotes may be used, if possible. Biomaterials may be secreted, such as proteins and some biominerals; sequestered, such as metal ions or some biominerals; or accumulated within cells, such as silk, cotton, fibers, and bioplastics. Cells must be lysed to release biomaterials that accumulate within cells.

Typical microdeposition systems have a typical minimum droplet size in the picoliter range, which roughly corresponds to a droplet diameter of 10 µm. This is substantially larger than typical prokaryotes (about 1 µm for *E. coli*), on the small side for single-celled eukaryotic species, and much smaller than cells from most multicellular organisms.

Therefore, cell strains that may be used with presently available commercially available microdeposition systems can most easily be chosen from among *Saccharomyces cerevisiae, Schizosaccharomyces pombe*, and *Thalassiosire pseudonana. S. cerevisiae* is a common, spherical yeast about 5-10 µm in diameter. It grows very quickly, is robust under standard laboratory conditions, and has an extensive history of being genetically engineered. *S. pombe* is another common yeast, similar to *S. cerevisiae* in many respects. It is rod-shaped, however, which is less advantageous than a spherical shape. *T. pseudonana* is an often-studied diatom. It deposits silica, however, the ability to control and regulate silica deposition has not been established.

Print Medium

The printing medium must keep the cells alive and should keep them in a non-biomaterial-producing state before printing; provide protection during printing; not interfere with cell expression post-printing; and work together with the print substrate to form a physical support structure for the cells and to minimize cell motion (drift or migration) after printing. Microdispensing systems have a viscosity limit, which means the print medium must be printed in a near liquid state. If the print medium were to contribute to the physical support structure, it would have to be triggered to gel after printing.

The print medium used in the experiments described herein is detailed below. The basic recipe contains dextrose (i.e., D-glucose). In experiments involving an induced control, however, galactose was substituted at a 1:1 weight ratio. For a 300 ml final volume, 2.01 g yeast nitrogen base, 0.576 g yeast synthetic drop-out medium (uracil deficient), and distilled water to a total of 270 ml were combined and then autoclaved. If any other additives were required for a particular experiment, they were added before autoclaving, unless they would not survive autoclaving. After cooling the autoclaved mixture, 30 ml of sterile 20% glucose solution, 300 µl of a 1000× concentrated ampicillin solution, and any experiment-specific additives that would not have survived autoclaving, but had been sterilized by other means, were added. Finally, the print medium was stored at 4° C. until use.

Print Substrate

The print substrate provides several functionalities according to the present invention. The print substrate has to support and keep the cells alive after printing, allow (in combination with the print medium) for a sufficiently low level of cell "drift" post-printing, support the printed cells in an actively secreting state for long enough to allow a sufficient biomaterial yield, bind the secreted biomaterial so it can be isolated, and allow removal (washing away) of the cells post-secretion. An illustrative print substrate according to the present invention is as follows. For a 300 ml final volume, 2.01 g yeast nitrogen base, 0.576 g yeast synthetic drop-out medium (uracil deficient), 9 g agarose, and distilled water are combined for a total of 270 ml. If any other additives were necessary for a particular experiment, they were added, as well, unless they would not survive autoclaving. The combined ingredients are then autoclaved followed by cooling until the container was cool to the touch. Then, 30 ml of a sterile 20% galactose solution and 300 µl of a 1000× concentrated ampicillin solution were added, as were any experiment-specific additives that would not have survived autoclaving, which were sterilized by other means. The liquid substrate mixture was then poured into petri dishes using sterile technique, and the agarose was permitted to gel. The plates were then stored at 4° C. until use.

3D Printing System

Additive manufacturing systems are typically comprised of two major parts: a dispensing subsystem, which handles feeding the biomaterial at the appropriate rate and time, and a positioning subsystem, which deposits the biomaterial at a preselected location. In some designs, the positioning subsystem is physically integrated with the dispenser and moves it relative to a stationary platform on which the finished piece is deposited. In others, the positioning subsystem moves the platform, the dispenser head is stationary, and only software integration is required between the two.

There are a number of commercially available microdispensing systems capable of printing living cells at picoliter resolution, which corresponds to a droplet diameter of about 10 µm. Spatial resolution of positioning systems is typically finer: about 1-2 µm for DC-motor-based solutions, and into the nanometers for piezo-based systems.

In the experiments described herein, selected dispensing system requirements included a combination of dispensing hardware, dispensing verification sensors (e.g., camera), controller/drive electronics, and software, some or all of which may be integrated with each other, sufficient to allow commanded dispensing to the following specifications:

(1) dispense droplets of ≤50 µl to 100 µl,
(2) fluid reservoir of ≥25 µl,
(3) reliably load and dispense fluids containing particulates ≥10 µm in diameter,
(4) compatibility with fluids having a viscosity ≥0.9 mPa·s at a temperature of 5-40° C.,
(5) droplet throughput ≥5 Hz,
(6) no bio-incompatible wetted parts,
(7) dispenser head empty/clean/reload cycle time ≤1 hour,
(8) controllable via a direct interface (e.g., serial) or triggered via an external signal (to allow for synchronization with positioning system timing),
(9) command interface compatible with real-time operation,

(10) accept direct, low-level commands to trigger dispensing, query dispensing status, or dispensing complete signal,
(11) compatible with external hardware mounting of position subsystem and printing substrate,
(12) accept commands via the same software as the positioning subsystem,
(13) including droplet sensing/metrology system (e.g., focused optical feed to CCD) to allow software to perform droplet verification analysis and adjustment.

The commercially available MicroDrop MD-E-6010 (MicroDrop Technologies GmbH, Dorderstedt, Germany), was deemed to meet these specifications and, thus, was selected for the work described herein.

Selected printing system requirements included a combination of motion positioners, motion verification sensors (encoders), controller/driver electronics, and software, some or all of which may be integrated with each other, sufficient to allow commanded positioning to the following specifications:

(1) range of motion in the X direction (along the print substrate surface) ≥10 mm,
(2) range of motion in the Y direction (along the print substrate surface, perpendicular to X)≥10 mm,
(3) range of motion in the Z direction (perpendicular to the print substrate surface) ≥10 mm,
(4) resolution (encoder or other sensor limit)≤0.01 μm,
(5) minimal incremental motion ≤0.1 μm,
(6) positional inaccuracy (measured directly, or inferred from maximum of roll/pitch/yaw at 10 mm, as on-axis bi-directional repeatability, compensated backlash, or equivalent figure)≤2 μm per 1 mm travel,
(7) controller/driver interface allowed for direct, low-level commands (e.g., via command-line interface),
(8) controller/drive interface specifications compatible with real-time operation,
(9) command set for controller/drive is well-documented and documentation is available,
(10) Linux (Debian is advantageous) support for controller/driver,
(11) compatible with external hardware mounting of dispensing subsystem and printing substrate,
(12) accepts commands via the same software as the dispensing subsystem.

The Physik International C-863.11/M-111.1DG (Physik Instrumente GmbH & Co. KG, Karlsruhe, Germany) controller/motor subsystem was selected for the experiments described herein.

Figure 3:
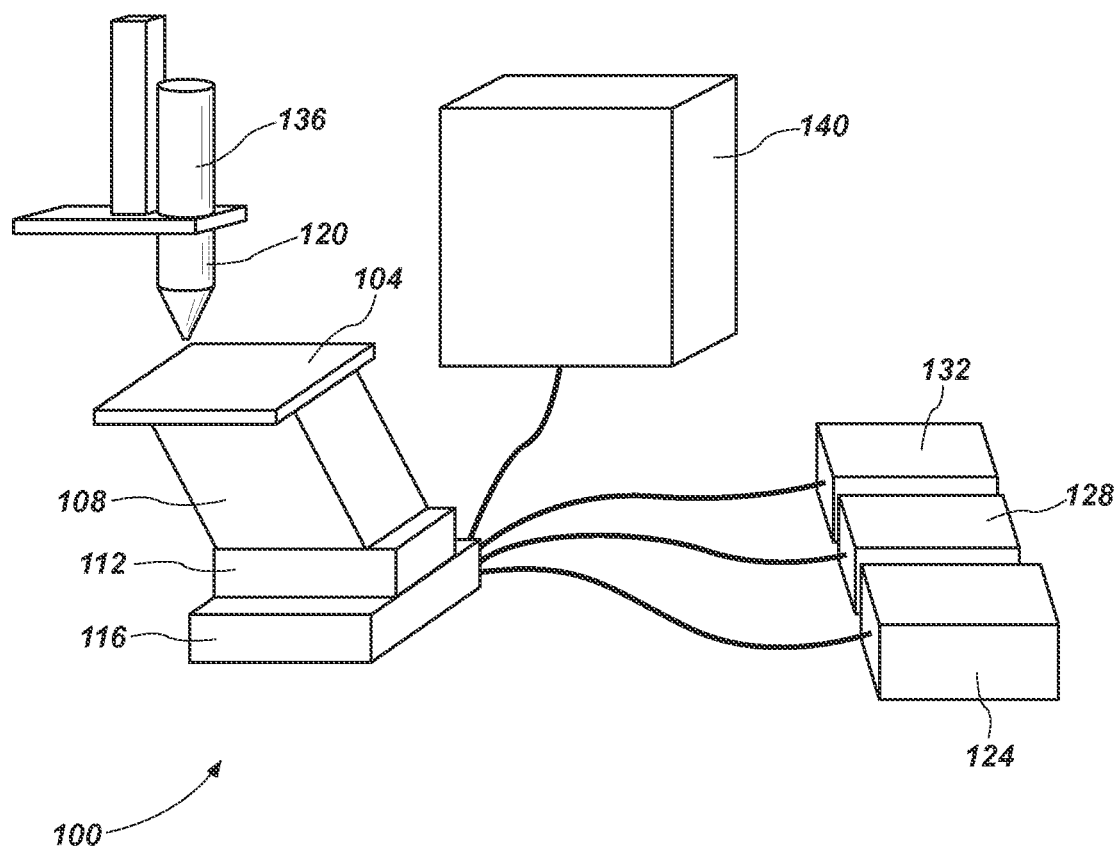
FIG. 3 shows a diagrammatic representation of an illustrative system for producing a three-dimensional biomaterial product.

FIG. 3 shows a diagrammatic representation of an illustrative micropositioning and microdeposition system 100 according to the present invention. A cell deposition platform 104 receives the printing substrate. The cell deposition platform 104 is positioned relative to a piezoelectric dispenser 120 by micropositioning axis stages 108, 112, and 116, which control the movement of the cell deposition platform 104 in the X, Y, and Z directions. Positioning controllers 124, 128, and 132 control the movement of the micropositioning axis stages 108, 112, and 116. Cells to be deposited on the printing substrate are held in a cell suspension reservoir 136 before being deposited by the piezoelectric dispenser 120. A pressure controller 140 is connected to the piezoelectric dispenser 120 for controlling the deposition of the cells.

Figure 4:
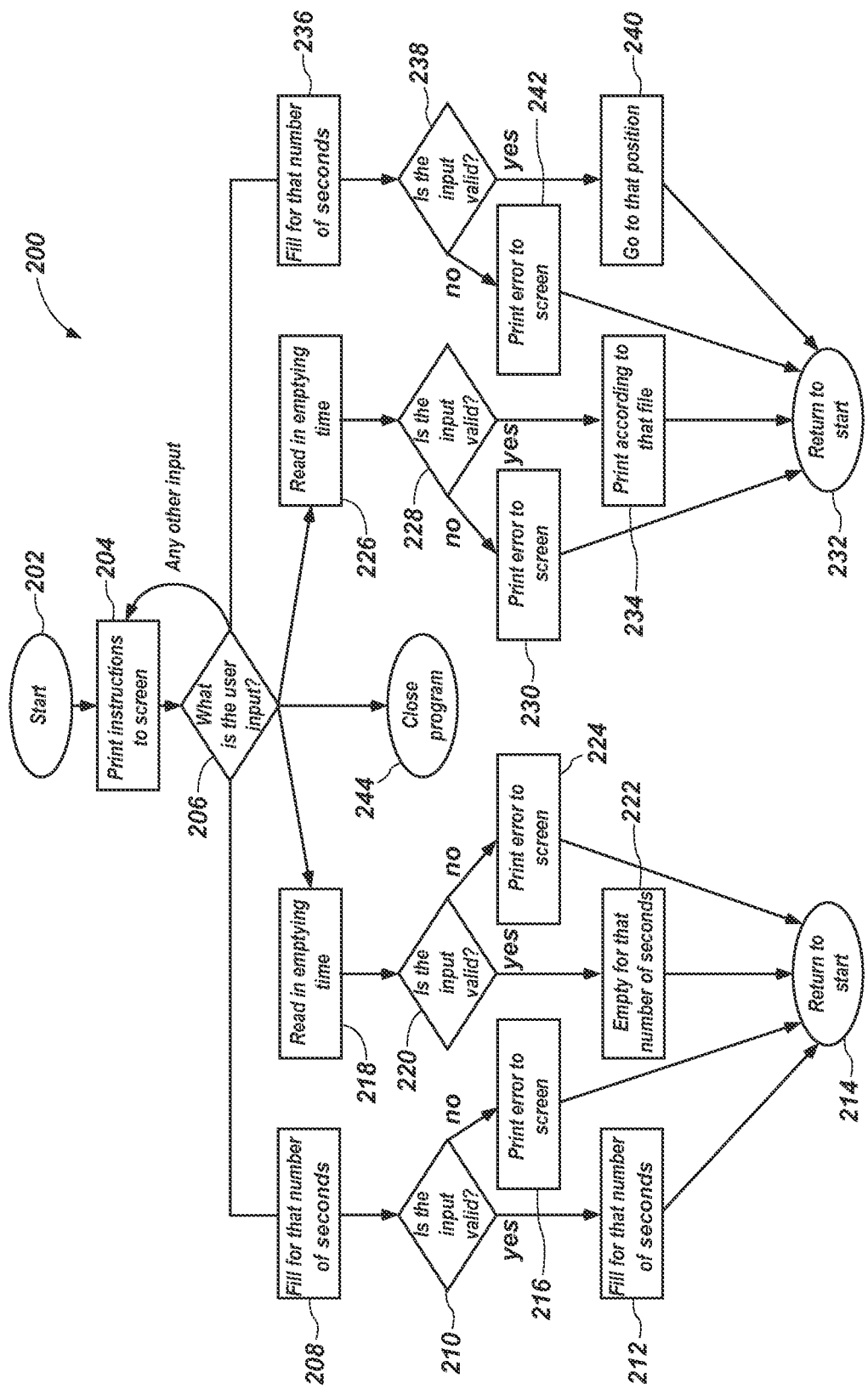
FIG. 4 shows a flow chart showing control of the dispensing and positioning subsystems of an illustrative system for producing a three-dimensional biomaterial product.

FIG. 4 shows a flowchart 200 for software that was written for this work, which takes real-time input from the user to fill and empty the dispenser head, and reads the input files that describe the pattern to be printed. It then sends the appropriate commands to the bioprinter, with separate serial port connections for the dispensing system and the position system. These input files include the XYZ locations where drops are to be deposited, the number of drops at each location, and the voltage and pulsewidth that the piezoelectric dispenser head will use. This software was written in C++ and runs on a Debian PC connected via RS-232 serial ports to the controllers for the positioning and dispensing systems. This software relies on raw user-supplied biomaterial patterns files. In an alternative illustrative embodiment, the software can be written to allow it to read 3D file formats that are more standard.

The program starts 202 by printing the inputted instructions to the display screen 204. The program then determines what the user input is 206. Next, the fill time for the bioprinter is read 208. If the input is valid 210, then the bioprinter will fill for the inputted number of seconds 212 before returning to start 214. If the input was not valid 210, then an error message is printed to the display screen 216 before returning to start 214.

The program continues by again printing the instructions to the display screen 204 and determining the user input 206. Then, the emptying time for the bioprinter is read 218. If the input is valid 220, then the bioprinter will empty for the inputted number of seconds 222 before returning to start 214. If the input was not valid 220, then an error message is printed to the display screen 224 before returning to start 214.

The program continues by once again printing the instructions to the display screen 204 and determining the user input 206. Next, the text file that the printing is to print from is read 226. If the input is valid 228, then printing is carried out according to the text file 234 before returning to start 232. If the input is not valid 228, then an error message is printed to the display screen 230 before returning to start 232.

The program continues still further by again printing the instructions to the display screen 204 and determining the user input 206. Next, the XYZ coordinates are read 236. If the input is valid 238, then the dispenser is directed to go to the indicated position 240 before returning to start 232. If the input is not valid 238, then an error message is printed to the display screen 242 before returning to start.

After all the inputted instructions have been carried, then the program closes 244.

EXAMPLES

The invention described herein is not limited to the particular configurations, process steps, and materials disclosed in the following examples. The examples set forth herein are merely illustrative of particular embodiments since the scope of the present invention will be limited only by the appended claims and equivalents thereof.

Example 1

*S. cerevisiae* was selected as a model organism for testing the concept of the present invention. A commercially available plasmid backbone, pYES2.1/V5-His-TOPO®, from Life Technologies (Carlsbad, Calif.) is specialized for use in *S. cerevisiae* and includes several features advantageous for this work. A green fluorescent protein coding sequence (modified from B. P. Cormack et al., Yeast-enhanced green fluorescent protein (yEGFP): a reporter of gene expression in *Candida albicans,* 143 Microbiology 303-311 (1997)), yeGFP, was inserted into pYES2.1N5-His-TOPO® using the TOPO TA cloning kit (Life Technologies) according to the instructions provided with the kit.

The pYES2.1/V5-His-TOPO® plasmid contains a GAL1 promoter for induction of expression of a cloned protein-coding sequence in the presence of galactose as a carbon source. Expression is suppressed in the presence of glucose as a carbon source. The plasmid also contains a TOPO®Cloning site for insertion of the coding sequence of interest, a V5 epitope, a polyhistidine (6×His) region, a CYC1 transcription termination signal, a pUC origin of replication for plasmid replication in *E. coli*, an ampicillin resistance gene for plasmid selection, a URA3 promoter and URA3 gene for selection in yeast strains unable to otherwise grow in the absence of uracil, and a 2nd origin for plasmid replication in yeast.

Example 2

The procedure of Example 1 was followed except that a red fluorescent protein, yeRFP, coding sequence (mod. From 53 S. Keppler-Ross et al., A new purple fluorescent color marker for genetic studies in *Saccharomyces cerevisiae* and *Candida albicans*, 179 Genetics 705-710 (2008)) was inserted into the pYES2.1N5-His-TOPO® plasmid backbone.

Example 3

A secretion signal protein coding sequence (M. Clements et al., Secretion of human epidermal growth factor from *Saccharomyces cerevisiae* using synthetic leader sequences, 106 Gene 267-271 (1991)) shown to work for a wide variety of proteins in *S. cerevisiae* was inserted upstream of the respective yeGFP and yeRFP coding sequences of the plasmids of Examples 1 and 2. Upon expression, the signal sequence is attached to the protein of interest and signals the cell that the protein should be secreted. The signal sequence is cleaved as part of the secretion process, leaving expressed protein deposited intact in the extracellular environment. The nucleotide sequence for this signal sequence was modified slightly to account for limitations in available synthesis capabilities. The secretion signal sequence was added using Golden Gate assembly (C. Engler et al., Golden gate shuffling: a one-pot DNA shuffling method based on type IIs restriction enzymes, 4 PloS ONE e5553 (2009)).

Example 4

Since the yeGFP and yeRFP would need to be expressed in *E. coli* to provide a baseline for protein quantification, a consensus ribosome binding site (M. B. Elowitz & S. Leibler, A synthetic oscillatory network of transcriptional regulators, 403 Nature 335 (2000); V. Singh, Recent advancements in synthetic biology: current status and challenges, 535 Gene 1-11 (2014)) was added to the plasmids of Example 3 by site-directed plasmid mutagenesis (H. Liu & J. Naismith, An efficient one-step site-directed deletion, insertion, single and multiple-site plasmid mutagenesis protocol, 8 BMC Biotechnology 91 (2008)).

Example 5

The plasmids of Example 4 were separately inserted into ura3 *S. cerevisiae* cells, according to transformation methods well known in the art, and were selected on uracil-deficient medium. The functionality of the engineered cell strains was tested qualitatively by fluorescence microscopy. Both RFP and GFP were strongly expressed when grown on galactose medium, where the GAL1 promoter was induced, and only weakly expressed on glucose medium, where the GAL1 promoter was suppressed.

Figure 2:
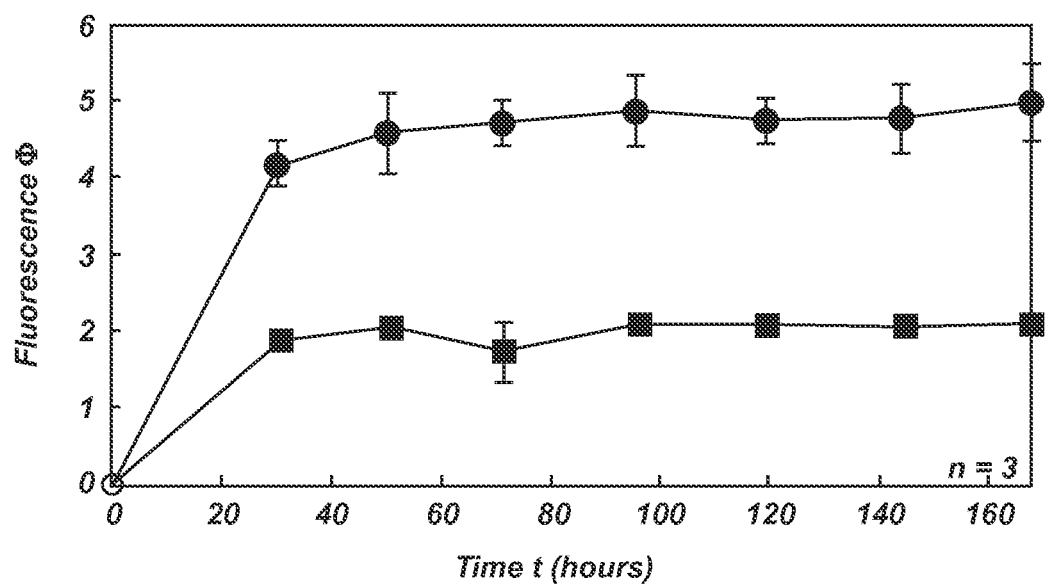
FIG. 2 shows extracellular GFP (green fluorescent protein) expression in transformed *Saccharomyces cerevisiae* cells as a function of time in the presence of dextrose (■) or galactose (●).

The transformants were then tested to quantify expression and demonstrate secretion. RFP and GFP cultures were grown with either glucose or galactose as the carbon source for seven days. Each day the cell density and fluorescence were measured and recorded. Dividing the fluorescence by the cell density gave an average measure of fluorescent protein produced per cell. In addition, each day an aliquot of cells from the cultures was taken, the cells removed, and the cell-free media tested for fluorescence to determine how much fluorescent protein was being secreted into the culture medium as opposed to simply being contained in cells. The fluorescence measurements were normalized to a fluorescent standard and then divided by the number of cells present in the sample to calculate $\Phi$, a measure of the average amount of secreted fluorescence per cell. The results for RFP and GFP are shown in FIGS. 1 and 2, respectively. These results show that significantly more fluorescent protein is secreted into the medium after induction with galactose than in cultures where expression was suppressed with glucose.

Example 6

The microdispensing system selected for these experiments had a viscosity limit of 10 cP (=10 mPa·s). Potential gelling agents, polyethylene glycol, glycerol, alginate, and agarose, for use in the printing medium were tested at different concentrations under varying temperature conditions, as shown in Table 1.

TABLE 1

| Gelling Agent | | Viscosity (cP or mPa · s) |
| --- | --- | --- |
| PEG | 10%, 22° C. | 5.3 |
|  | 10%, 30° C. | 4.8 |
|  | 20%, 29° C. | 12 |
|  | 20%, 38° C. | 12 |
| Glycerol | 25%, 22° C. | 2.2 |
|  | 50%, 21° C. | 6.8 |
|  | 100%, 21° C. | 12 |
|  | 25%, 27° C. | 12 |
|  | 50%, 39° C. | 4.3 |
| Alginate | 0.5%, 22° C. | 3.7 |
|  | 0.75%, 22° C. | 5.4 |
|  | 1.50%, 22° C. | 6.6 |
| Agarose | 1.0%, 21° C. | 1.3 |
|  | 0.5%, 32° C. | 3.0 |

Agarose and alginate yielded the most suitable viscosities in the range of concentrations that suited these experiments. Agarose gels below a threshold temperature, while alginate gels in the presence of calcium ions. Alginate was selected as a model print medium gelling agent, since adding temperature control to the printing process was not practical under the experimental conditions. Because calcium exposure can be provided by printing the medium onto a calcium-containing substrate, this selection provided function unification between the act of printing and the substrate gelling, thus simplifying the process.

Example 7

To determine whether the print medium had any negative effect on cell growth, RFP-expressing cells, GFP-expressing cells, and the original unaltered cell strain were grown in the print medium for a week, and cell density was measured. Neither the print medium nor the presence of the genetic modifications affected cell growth.

Example 8

To determine whether the print medium containing glucose would suppress biomaterial production, and whether the equivalent galactose concentration in the print substrate would induce it, the cell strains were grown in either the glucose-containing print medium or a modified version that instead contained galactose. As shown in FIGS. 1 and 2, the effects of glucose in suppressing biomaterial expression and galactose in inducing biomaterial expression were clearly shown. The "leakage" expression of GFP is about twice that of RFP, and RFP appears to be more stable than GFP, since it takes longer for GFP to accumulate to a steady level.

Example 9

Since positioning of the cells on the print substrate is an aspect of the present invention, quantifying and reducing uncertainty in positioning was studied. A goal of one cell per voxel was selected, thus keeping cell drift after printing to within one cell diameter, or about 10 microns, for *S. cerevisiae* was targeted.

A qualitative experiment comparing cell motion in ordinary aqueous medium to that in different gelling agents (glycerol, agarose, and alginate—with and without calcium) on an agar substrate was conducted to determine the amount of post-printing cell drift likely to occur. Videos taken at 200× magnification showed that baseline cell drift for cell printed in aqueous medium was some several hundred micrometers. The presence of agarose in the medium reduced cell drift to essentially zero, since it gelled completely upon cooling. Glycerol reduced drift about ten-fold. Alginate's effect without calcium was barely noticeable. Alginate with calcium, like agarose, gelled after printing and reduced cell drift to nearly an undetectable level. Thus, the alginate-based print medium reduced cell drift to acceptable parameters.

Example 10

To optimize the print resolution, a range of voltages and pulsewidths were tested for the piezoelectric dispenser head. Of the values tested, the maximum number of cells per drop was achieved with 150 V and a 150 µs pulsewidth. Lower voltages proved unreliable. For example, no droplet dispensed at all at 50 V.

The parameters that maximized the number of cells per drop appeared to be the most consistent in terms of standard deviation. Therefore, for reliable single-cell resolution it was decided to use the same parameters (150 V, 150 µs) that yielded the maximum number of cells per drop, but with more dilute cell cultures.

Example 11

The microdispensing system selected for this work was a contactless piezoelectric system that works by sending a pressure wave through a thin glass tube containing the cell culture. To ensure that the deposition process did not damage the transformed yeast cells, a lower limit for the viability of dispensed cells was determined using SYTOX Green (Life Technologies), a nucleic acid stain that can only enter cells with compromised membrane integrity, thus generally nonviable. A control of dead cells was prepared by placing a 1 ml aliquot of cell culture suspended in PBS (0.01 M $Na_2HPO_4$, 0.15 M NaCl, pH 7.2) in a 70-80° C. water bath for 10 minutes. Aliquots of 25 µl of cell culture at the same density in the same buffer was then printed into a sample container. Both the printed cells and the control cells were stained with 5 µM SYTOX Green following the manufacturer's protocols. The entire 25 µl printed samples and 25 µl of control were then each diluted into 200 µl of PBS to reduce background fluorescence. The 200 µl samples were then measured in a fluorometer to determine the amount of bound fluorescence, and then in a spectrophotometer to determine the cell density, which allowed calculation of the amount of fluorescence per cell.

The results indicated that there was a minimum survival rate of 40% for RFP-expressing yeast and 60% for the GFP-expressing yeast. While the true survival rate is likely to be substantially higher, these results demonstrate that enough cells survive deposition conditions to proceed with further experiments.

Example 12

To test that cells would be able to produce sufficient amounts of biomaterial after printing, growth and fluorescence of cells manually deposited on a print substrate were assayed. The print substrate had to keep the cells alive after printing, allow (in combination with the print medium) for a sufficiently low level of cell "drift" post-printing, support the printed cells in an actively secreting state for long enough to allow a sufficient biomaterial yield, bind the secreted biomaterial so it could be isolated, and allow removal (washing away) of the cells post-secretion. The print substrate contained agarose as the gelling agent, because it had acceptably low interference with fluorescence detection. The selection of a ura3 host strain meant uracil was required together with selective amino acid supplements as a selective nutrient source. Use of a galactose promoter meant the substrate had to contain galactose to induce expression. The choice of alginate as a biocompatible physical support meant the substrate had to contain calcium chloride to cause contact gelling. The open-air nature of the print process meant that ampicillin was necessary to prevent bacterial contamination. Finally, the initial choice of polyhistidine tags as biomaterial binding sites meant the substrate also needed to contain nickel ions.

Cell growth in the presence of galactose was delayed as compared to growth in glucose, but otherwise there were no other ill effects from using galactose as the carbon source. The presence of calcium ions appeared to have no negative effect on biomaterial production. The presence of nickel ions, however, was harmful at all but low concentrations.

Example 13

Polyhistidine tag binding tests for RFP and GFP were carried out using the Dynabeads His-Tag Isolation and Pull-Down Kit (Life Technologies). The proteins were bound to the beads, washed, and then eluted, and then the eluted products were separated electrophoretically on a polyacrylamide gel. Unique bands of appropriate molecular weight were detected in the eluted products, but not in the lysis solutions, flow through, or wash solutions. Also, wild type yeast failed to produce the unique bands. These results demonstrate that the combination of quantity of tagged biomaterial (protein) produced in the transformed yeast cells and the binding efficiency of the tags were sufficient for detection.

However, the Dynabead kit uses cobalt as a binding substrate, and the amount of cobalt needed in a print substrate for comparable binding was well above the toxicity threshold for yeast cells. Therefore, binding polyhistidine tags using metal (nickel or cobalt) ions is not optimal.

Example 14

In this prophetic example, the process of Example 13 is repeated except that binding of the RFP and GFP proteins is carried out by antibody binding instead of metal binding.

Example 15

The RFP- and GFP-expressing yeast of Example 5 were printed in an alternating pattern on the substrate of Example 12. The droplets were placed at 0.4 mm increments for a 0.8 mm×0.8 mm grid. Micrographs of the resulting grid were taken with a fluorescence microscope using a different filter to view each fluorescent protein. Red fluorescence was detected from the sites where RFP-expressing cells were deposited, and green fluorescence was detected from the sites where GFP-expressing cells were deposited.

In the foregoing Detailed Description, various features of the present disclosure are grouped together in a single embodiment for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description of the Disclosure by this reference, with each claim standing on its own as a separate embodiment of the present disclosure.

It is to be understood that the above-described arrangements are only illustrative of the application of the principles of the present disclosure. Numerous modifications and alternative arrangements may be devised by those skilled in the art without departing from the spirit and scope of the present disclosure and the appended claims are intended to cover such modifications and arrangements. Thus, while the present disclosure has been shown in the drawings and described above with particularity and detail, it will be apparent to those of ordinary skill in the art that numerous modifications, including, but not limited to, variations in size, materials, shape, form, function, and manner of operation, assembly, and use may be made without departing from the principles and concepts set forth herein.

The subject matter claimed is:

1. A method for producing a three-dimensional biomaterial product, the method comprising:
(A) providing a 3D printing system comprising a cell suspension reservoir, a piezoelectric dispenser, and a cell deposition platform, wherein the cell suspension reservoir and the cell deposition platform are physically separated;
(B) providing living cells configured for secreting a selected biomaterial;
(C) providing a suppressing print medium that comprises a substance that suppresses the living cells from secreting the selected biomaterial upon contact with the living cells, wherein the substance that suppresses the living cells from secreting the selected biomaterial comprises glucose;
(D) dispersing the living cells in the suppressing print medium to create a cell-medium mixture;
(E) placing the suppressing print medium and the living cells into the cell suspension reservoir;
(F) providing a substrate that (1) comprises a gelling agent; (2) comprises a substance providing a substrate that (1) comprises a gelling agent; (2) comprises a substance that overcomes the suppression of the suppressing print medium and induces the secretion of the selected biomaterial from the living cells upon contact with the living cells, wherein the substance that overcomes the suppression of the suppressing print medium and induces secretion of the selected biomaterial comprises galactose; and (3) is configured to bind to the selected biomaterial upon contact with the cell-medium mixture after the secreting;
(G) placing the substrate on the cell deposition platform;
(H) contacting the suppressing print medium, the living cells, and the substrate by 3D printing the cell-medium mixture from the cell suspension reservoir onto the cell deposition platform using the piezoelectric dispenser containing the substrate in a predetermined three-dimensional pattern;
(I) causing, by the contacting of the living cells and the substrate by the 3D printing, the living cells to overcome the suppression of the suppressing print medium and to secrete the selected biomaterial from the living cells in sufficient amount to bind to the substrate; and
(J) causing, by the contacting of the suppressing print medium and the substrate, the print medium to form a gel upon contact with the gelling agent in the substrate, wherein the gel minimizes cell drift such that the predetermined three-dimensional pattern is maintained; and
(K) causing, by the contacting of the selected biomaterial and the substrate, the selected biomaterial to bind to the substrate, wherein the amount of the selected biomaterial is sufficient to bind to the substrate; and
(L) separating the cells from the bound biomaterial to result in the three-dimensional biomaterial product.

2. The method of claim 1 wherein the biomaterial is expressed by an inducible promoter.

3. The method of claim 2 wherein the inducible promoter is induced by galactose.

4. The method of claim 1 wherein the living cells comprise *Saccharomyces cerevisiae*.

5. The method of claim 1 wherein binding of the biomaterial to the substrate comprises antibody-antigen binding.

6. The method of claim 1 wherein separating the cells from the bound biomaterial comprises washing the bound biomaterial.

7. The method of claim 1 further comprising:
(M) separating the biomaterial product from the substrate.

8. The method of claim 1 wherein the biomaterial comprises a protein.

9. The method of claim 1, wherein the maximum resolution of the 3D printing system is realized when a single cellular unit is contained in each voxel of cell-medium mixture printed.

10. The method of claim 1, wherein the suppressing print medium comprises alginate and wherein the substrate contains the gelling agent calcium, the calcium causing the print medium to form a gel after depositing.

11. The method of claim 1, wherein the depositing step is performed by a 3D printing system using a voltage of 150 V and a pulse of 150 μs.

12. The method of claim 1, wherein the substrate contains a selective nutrient source that maintains survival of the living cells after the depositing.

13. The method of claim 1, wherein the 3D printing system is configured to deposit a volume of print medium at a pre-determined location in three dimensional space.

14. The method of claim 3, wherein the suppressing print medium comprises 30 ml of a sterile 20% glucose solution for every 300 ml of the print medium.

15. The method of claim 3, wherein the substrate comprises 30 ml of a sterile 20% galactose solution for every 300 ml of the substrate.

16. The method of claim 1, wherein the piezoelectric dispenser is compatible with fluids having a viscosity of 0.9 mPa·s at a temperature of 4 to 40° C.

17. The method of claim 1, wherein the living cells are the cells of eukaryotic microorganisms.

18. The method of claim 1, wherein the step of placing the suppressing print medium and the living cells into the cell suspension reservoir occurs either before or after the dispersing.

* * * * *